(12) United States Patent
Samolyk

(10) Patent No.: US 9,327,066 B2
(45) Date of Patent: *May 3, 2016

(54) CPB SYSTEM WITH DUAL FUNCTION BLOOD RESERVOIR

(71) Applicant: Keith Samolyk, Windsor, CT (US)

(72) Inventor: Keith Samolyk, Windsor, CT (US)

( * ) Notice: Subject to any disclaimer, the term of this patent is extended or adjusted under 35 U.S.C. 154(b) by 91 days.

This patent is subject to a terminal disclaimer.

(21) Appl. No.: 13/798,484

(22) Filed: Mar. 13, 2013

(65) Prior Publication Data

US 2014/0271356 A1  Sep. 18, 2014

(51) Int. Cl.
| A61M 1/00 | (2006.01) |
| A61M 1/10 | (2006.01) |
| A61M 1/16 | (2006.01) |
| A61M 1/36 | (2006.01) |

(52) U.S. Cl.
CPC .............. *A61M 1/101* (2013.01); *A61M 1/1698* (2013.01); *A61M 1/3621* (2013.01); *A61M 1/3627* (2013.01); *A61M 1/3666* (2013.01)

(58) Field of Classification Search
CPC ............ A61M 1/3666; A61M 1/3621; A61M 1/1698; A61M 1/3627; A61M 1/32; A61M 1/34; A61M 1/101; A61M 1/3603; Y10S 128/03; Y10S 261/28
USPC .................................. 422/44; 604/6.01–6.14
See application file for complete search history.

(56) References Cited

U.S. PATENT DOCUMENTS

| 5,055,198 | A | | 10/1991 | Shettigar |
| 5,490,763 | A | * | 2/1996 | Abrams ..................... F04D 5/00 415/206 |
| 5,650,071 | A | | 7/1997 | Brugger et al. |
| 5,858,238 | A | * | 1/1999 | McRea et al. .................. 210/645 |
| 5,928,178 | A | * | 7/1999 | Samolyk ....................... 604/6.15 |
| 6,306,346 | B1 | | 10/2001 | Lindsay |
| 6,579,257 | B1 | * | 6/2003 | Elgas et al. ...................... 604/67 |
| 6,827,898 | B1 | | 12/2004 | Fausset et al. |
| 8,409,846 | B2 | | 4/2013 | Hassanein et al. |
| 2002/0044889 | A1 | | 4/2002 | Aboul-Hosn et al. |
| 2002/0147440 | A1 | | 10/2002 | Samolyk |
| 2006/0009728 | A1 | * | 1/2006 | Litzie et al. ................... 604/6.14 |
| 2006/0089586 | A1 | * | 4/2006 | Kaus .................... A61M 1/3666 604/4.01 |
| 2009/0048554 | A1 | | 2/2009 | Nogueira Sanches et al. |
| 2009/0076433 | A1 | * | 3/2009 | Folden ................ A61M 1/3643 604/4.01 |
| 2009/0099498 | A1 | | 4/2009 | Demers et al. |
| 2009/0221949 | A1 | * | 9/2009 | Allers et al. .................. 604/6.16 |
| 2009/0275875 | A1 | * | 11/2009 | Liebing et al. ............... 604/6.09 |
| 2011/0040229 | A1 | * | 2/2011 | Hannan et al. ............... 604/6.11 |
| 2011/0208108 | A1 | * | 8/2011 | Muller-Spanka et al. ... 604/6.09 |

(Continued)

*Primary Examiner* — Tatyana Zalukaeva
*Assistant Examiner* — Ariana Zimbouski
(74) *Attorney, Agent, or Firm* — Alix, Yale & Ristas, LLP

(57) ABSTRACT

The venous reservoir is omitted from an extracorporeal blood circuit system by substituting a blood reservoir in parallel with the arterial pump. The reservoir has an inlet connected to the outlet of the pump and an outlet connected to the inlet of the pump. At least three blood flow paths can be configured. A main path has the inlet and outlet of the reservoir blocked while pumped blood flows through the venous cannula, the oxygenator, and the arterial cannula. An accumulator path has the inlet to the oxygenator and the outlet of the reservoir blocked while blood flows through the venous cannula and the inlet to the reservoir. A discharge path has the inlet of the reservoir blocked while the outlet is open whereby blood from the reservoir flows into the oxygenator. In a fourth configuration, the ECC fluid can be recovered in the reservoir and hemoconcentrated for autologous transfusion.

19 Claims, 13 Drawing Sheets

(56) References Cited

U.S. PATENT DOCUMENTS

| | | |
|---|---|---|
| 2011/0238029 A1 | 9/2011 | Biset et al. |
| 2013/0012909 A1* | 1/2013 | Pinto .............................. 604/406 |
| 2013/0338561 A1* | 12/2013 | Wieting et al. .............. 604/6.09 |

\* cited by examiner

CPB SYSTEM WITH DUAL FUNCTION BLOOD RESERVOIR

BACKGROUND OF THE INVENTION

The present invention relates to medical equipment, techniques and procedures, and more particularly, to the circulation and recovery of blood during and immediately following heart bypass and similar surgery involving a cardiopulmonary bypass circuit (CPB) or more generally, an extracorporeal blood circuit (ECC).

A persistent dilemma is faced thousands of times each day worldwide, of how to handle the volume of a patient's blood in the ECC after the surgical procedure has been completed and the patient is disconnected from the circuit.

One option is to transfuse the volume in the circuit to the patient, in the manner of a blood transfusion, without compromising the integrity of the bypass system. It should be appreciated that the circuit includes a crystalloid priming fluid which is necessary to initiate the pumping of the circuit. Therefore, transfusion of the content of the circuit would include transfusion of the priming solution which, by the end of the surgery, has been fully mixed with the patient's own blood. The hematocrit concentration is therefore low, i.e., approximately 18-25%. Although some such diluted blood can be transfused to the patient, a relatively large fraction of the volume of the circuit is not transfused, because this volume is needed to maintain the integrity of the circuit in the event full bypass is to be resumed. Also the patient's physiology can only accommodate a finite amount of volume before circulatory overload or TACO is exhibited with organ edema and dysfunction.

Alternatively, the content of the ECC circuit can be transferred to sterile blood bags, for a possible re-transfusion to the patient either in or out of the operating room. This option also suffers from a large amount of volume with the dilution of important blood components and the need to keep a substantial fraction of the diluted blood in the circuit to maintain circuit integrity.

Yet a third option, is to chase all the volume in the ECC circuit with a crystalloid solution to a so-called "cell washer", where the fluid volume is separated into red blood cells and effluent. Although the red blood cells are saved, the effluent is deemed waste and therefore discarded, yet the effluent contains many desirable constituents of whole blood, such as plasma, platelets, clotting factors, albumin, proteins, etc.

Finally, the most straight-forward option is to seal or drain and discard the content of the ECC circuit. This is common in pediatric open heart cases, but benefits neither the patient nor anyone else, and presents a significant disposal problem to the perfusionist (i.e., the operator of the heart/lung machine), who must clean up and discard this wasted volume.

Because in the foregoing options, the patient cannot receive his own entire blood volume from the circuit immediately following cardiac, thoracic, or vascular procedures, if the need for additional blood arises, the only available source is from previously stored blood bags. If the patient gave blood prior to surgery, which is rare, then the patient could receive so-called autologous blood. Most often, however, such additional blood or blood products would be provided from a dwindling and precarious blood bank supply, which originated from an allogeneic (unknown) donor. Transfusing such blood can arouse anxiety and create problems including hemolytic reactions, immunological reactions blood viruses; vCJD or Prion's disease (BSE) and Trali or TACO. Human error can occur when mistakes are made by giving non-compatible or mislabeled blood products. Artificial blood substitutes or HBOC's can be used, but these are limited to carrying only oxygen, have a short half-life and do not compare favorably to the miraculous abilities of the patient's own blood. Lastly, there is also a small population of patients that completely refuse any foreign blood or blood products of any kind, due for example, to religious beliefs.

Because of these reasons, the need exists to reduce allogeneic blood use and strive for "bloodfree surgery" and the growing movement towards blood management.

Significant improvements toward achieving this goal have already been implemented using the Hemobag® techniques described in the present inventor's U.S. Pat. Nos. 5,928,178; 6,398,751; 7,033,334; and 7,402,278, the entire disclosures of which are hereby incorporated by reference. A substantial volume of concentrated whole blood can be quickly and easily recovered from the ECC immediately following, i.e., cardiac, thoracic, or vascular surgery. Most of the blood in the ECC flows into a blood reservoir, preferably a dedicated blood bag, and hemoconcentrated in the blood reservoir while connected in a sub circuit of the ECC.

In addition to the recovery of a patient's blood following surgery, a related concern is the management of the fluid or volume in the ECC and in the patient during surgery. The volume of fluid circulated to the patient during surgery over the course of several hours must be varied to correspond with the particular stages in the surgery and the patient's physiology. Make-up fluid or volume (crystalloid, colloid or blood product) is required when the overall need or blood concentration in the ECC and the patient needs correction for stabilization. This large amount of diluted blood increases the time necessary for recovery of the patient's whole blood after surgery.

Extracorporeal circuits can be necessary after surgery, for example in the critical intensive care unit (ICU) where the patient relies on the ECC for a period of days rather than hours (ECMO or VADS). The concentration of blood in the patient and the circuit, and the total volume of fluid in the patient plus the circuit can vary considerably, and it is important that the fluid volume management be closely monitored.

Presently, fluid management is rather varied and implemented by opening and closing clamps into and out of the venous reservoir of the ECC. Regardless of any other components that may be fluidly aligned, when the venous reservoir is fluidly connected in series in the fluid path along the cannula line from the patient and the cannula line to the patient, the venous reservoir acts imprecisely as an in-line accumulator of fluid or volume when the flow to the patient is to be decreased and as a source of fluid volume when flow to the patient is to be restored or increased.

SUMMARY OF THE INVENTION

It is an object of the present invention, to simplify and improve the efficiency of an extracorporeal blood circuit both in normal mode for circulating blood through the patient and in a subsequent mode for recovering concentrated whole blood from the circuit.

This simplification is achieved by eliminating the venous reservoir that is part of a conventional ECC, and substituting a blood reservoir that performs the fluid accumulation function of the venous reservoir and the blood recovery function of a blood bag where the fluid in the ECC system is collected or recovered and hemoconcentrated.

In one aspect, the present disclosure is directed to a system which provides for circulating a patient's blood as a fluid volume through the patient in an extracorporeal circuit having a first cannula line for fluid flow from the patient and a second cannula line for fluid flow to the patient. The volume of fluid flow from the first cannula line to the second cannula line is adjusted by selectively redirecting fluid flow between the first cannula line and the second cannula line into or out of a closed accumulator blood bag of substantially transparent, bio-compatible material, having upper and lower ends, and having a selectively open and closable accumulator inlet line from the first cannula, and a selectively open and closable accumulator outlet line to the second cannula. At the conclusion of the circulatory flow through the patient, a substantial volume of whole blood is recovered from the extracorporeal circuit, by (a) disconnecting the extracorporeal circuit from the patient; (b) flowing (including draining) at least most of the fluid remaining in the disconnected circuit, into the accumulator blood bag; (c) fluidly connecting a hemoconcentrator to the blood bag to form a recovery circuit; (d) circulating the fluid between the blood bag and the hemoconcentrator through the recovery circuit to increase the hematocrit concentration; and (e) when the hematocrit concentration of the fluid in the blood bag reaches a desired value, removing the blood bag from the recovery circuit for autologous reinfusion to the patient.

The preferred equipment includes a disposable pump tubing set for the extracorporeal blood circuit system. The tubing set comprises two inlet line branches and two outlet line branches for the pump. Most preferably, the inlet branches are fluidly connected to the pump by a common inlet tube and the outlet branches are fluidly connected to the pump by a common outlet tube, and each branch carries a clamp.

The tubing set and blood reservoir are preferably secured or securable in a modular fashion to a panel of a heart lung machine or similar ECC frame. A pump is attachable to a system inlet line for the pump to receive blood from the patient and a system outlet line for the pump to deliver blood to the patient. The pump tubing unit is connectable to the pump, with two inlet line branches fluidly connected to the pump inlet and two outlet line branches fluidly connected to the pump outlet, each branch having a free end that carries a Colder Quick type connector (hereinafter, "Colder") and a clamp between the pump and the respective Colder connectors. A blood reservoir unit having a support plate is mountable to the panel, and carries a blood bag having an inlet line with a free end and Colder connector and an outlet line with free end and Colder connector.

The preferred embodiment is directed to an extracorporeal blood circuit system (ECC) including a venous cannula line, an oxygenator in fluid communication with the outlet of the venous cannula, an arterial cannula line having an inlet in fluid communication with the outlet of the oxygenator and an outlet for delivering oxygenated blood to the patient, a pump having an inlet connected to the outlet of the venous line and an outlet connected to an inlet line of the oxygenator. A blood reservoir has an inlet line connected to the outlet of the pump and an outlet line connected to the inlet of the pump. Flow path control means such as clamps, selectively configuring at least three blood flow paths. A main path has the inlet and outlet lines of the blood reservoir blocked while pumped blood flows through the venous cannula line, the oxygenator, and the arterial cannula line. An accumulator path has the inlet to the oxygenator and the outlet line of the blood reservoir blocked while blood flows through the venous cannula line and the inlet line to the blood reservoir. A discharge path has the inlet line of the blood reservoir blocked while the outlet line of the blood reservoir is open whereby blood from the blood reservoir flows with pumped blood from the venous cannula line into the oxygenator and the arterial cannula line.

These three paths implement the function of the omitted venous reservoir, with a novel arrangement in which the pump inlet is connected to the outlet of the venous cannula line and the outlet of the blood reservoir, and the pump outlet is connected to the inlet line of the oxygenator and the inlet of the blood reservoir. Thus, unlike a conventional venous reservoir, the present blood reservoir has an inlet line connected to the outlet of the pump and an outlet line connected to the inlet of the pump. As a result, the blood reservoir is connected in parallel, not in series, with the blood flow path containing the venous cannula line, the arterial pump, and the oxygenator.

In this parallel path, the blood reservoir can readily be used for hemoconcentrating the fluid in or outside the ECC circuit after the case. If the blood reservoir includes an IV port, the blood reservoir with hemoconcentrated blood can be removed from the hemoconcentration circuit and used directly for autologous blood transfusion.

In the preferred embodiment the blood reservoir is a closed bag of substantially transparent, bio-compatible material, defining upper and lower ends. An outlet port is located at the lower end of the bag, an inlet port is located at the lower end of the bag, and an IV port is located at the lower end of the bag. The control means can be further configured for an additional, recovery path in which the venous cannula line and the oxygenator line are blocked while the blood reservoir inlet and outlet lines are open. A hemoconcentrator is fluidly connected between the outlet of the pump and the inlet line of the blood reservoir, thereby establishing a recirculating flow of blood between the blood reservoir and the hemoconcentrator.

BRIEF DESCRIPTION OF THE DRAWING

These and other objects and advantages of the invention will be evident to practitioners in this field, upon reading the following description in conjunction with the accompanying drawing, in which.

DESCRIPTION OF THE PREFERRED EMBODIMENT

Figure 1:
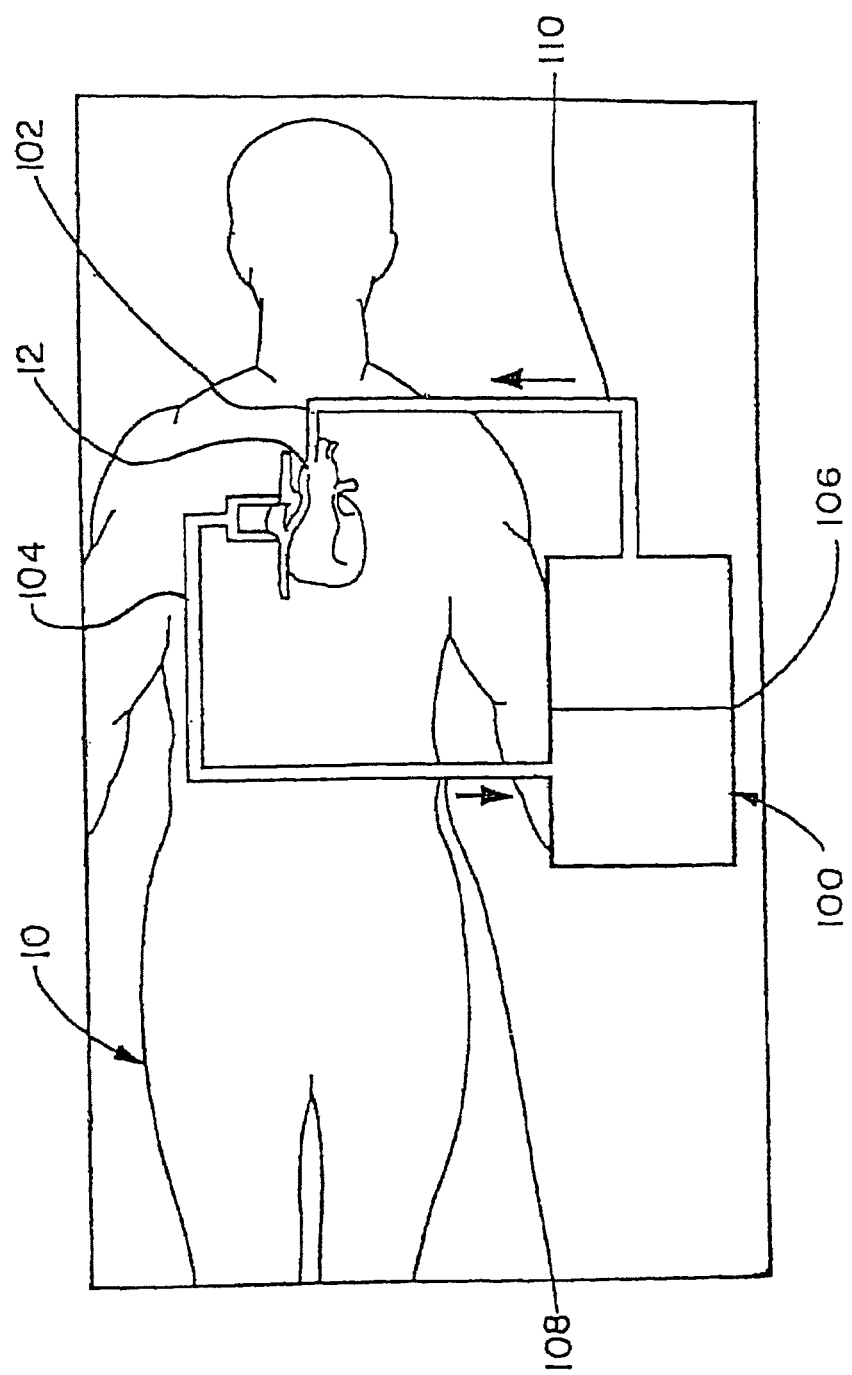
FIG. 1 is a schematic representation of a cardiopulmonary bypass system connected to a patient during surgery.

FIG. 1 schematically shows a patient 10 during heart bypass surgery, wherein a cardiopulmonary bypass (CPB) system, also known as a heart/lung machine 100, is connected to the patient's heart 12. The CPB system 100 includes an arterial cannula 102 inserted into the aorta at the heart 12 and a venous cannula 104 inserted into one or both of the vena cava. Arterial pump 106 (and associated components to be described hereinafter), receives deoxygenated blood from the venous cannula 104, via inlet line 108, and delivers externally oxygenated blood via outlet line 110, to the arterial cannula 102.

Figure 2:
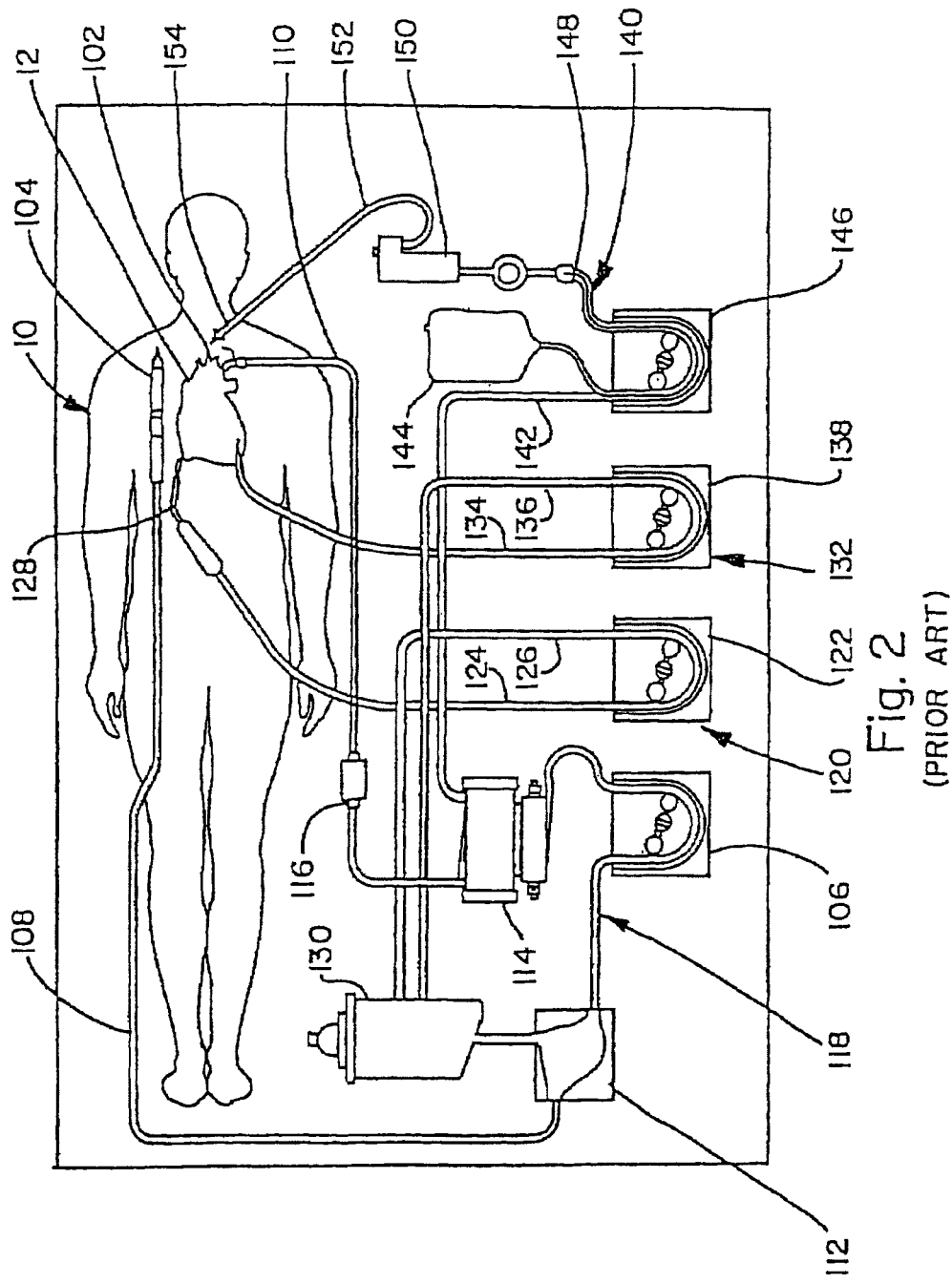
FIG. 2 is a schematic representation of a conventional bypass system, showing various fluid circuits as connected during surgery.

FIG. 2 shows additional details represented schematically, of one conventional arrangement by which the CPB system 100 is connected to the patient 10 during bypass surgery. Deoxygenated blood in the inlet line 108 enters a venous reservoir 112, which is fluidly connected to the arterial pump 106. The discharge from the pump 106 enters a heat exchanger and oxygenator 114, passes through an arterial filter 116, before eventually entering the arterial cannula 102. The components and lines 102-116, can be considered collectively, as defining a CPB circuit 118.

The CPB system 100 typically includes other circuits as well. A field suction circuit 120 includes a roller pump 122, a suction inlet line 124 to the pump 122, and a suction outlet line 126 which returns to the venous reservoir 112 (or optionally a cardiotomy reservoir 130 prior to the venous reservoir). The suction inlet 124 terminates in a so-called "field sucker" 128, by which bleeding at the field can be recovered during surgery.

Another circuit is the vent circuit 132, having a vent inlet line 134 leading to a roller pump 138, from which air and blood vented from the heart 12, can eventually be delivered via outlet line 136 to the venous reservoir 112 or cardiotomy reservoir 130.

A cardioplegia circuit 140 is typically present, whereby oxygenated blood can be selectively drawn from the oxygenator 114, via cardioplegia inlet line 142, into the cardioplegia pump 146, where cardioplegia solution from bag 144 can be mixed therewith, for delivery via cardioplegia outlet 148, to a cardioplegia processing unit 150. The processing unit 150 typically includes a heat exchanger, a bubble trap, and temperature and pressure monitor. The outlet line 152 from the unit 150 terminates in a cardioplegia cannula 154 or needle.

Figure 3:
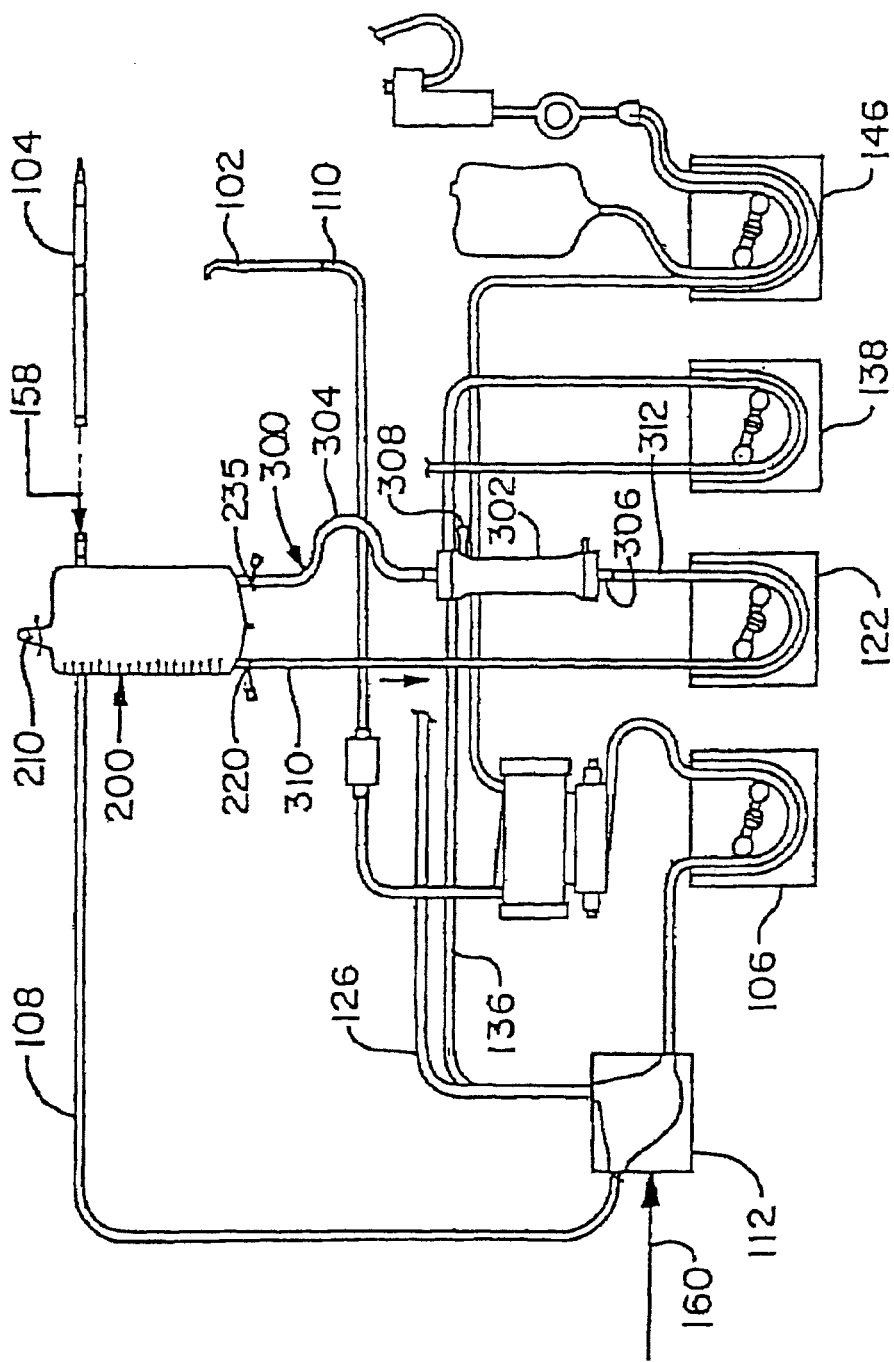
FIG. 3 is a schematic representation of how the circuits shown in FIG. 2 can be modified during a particular step of a blood recovery and hemoconcentration method according to the incorporated U.S. Pat. No. 5,928,178.
Figure 4:
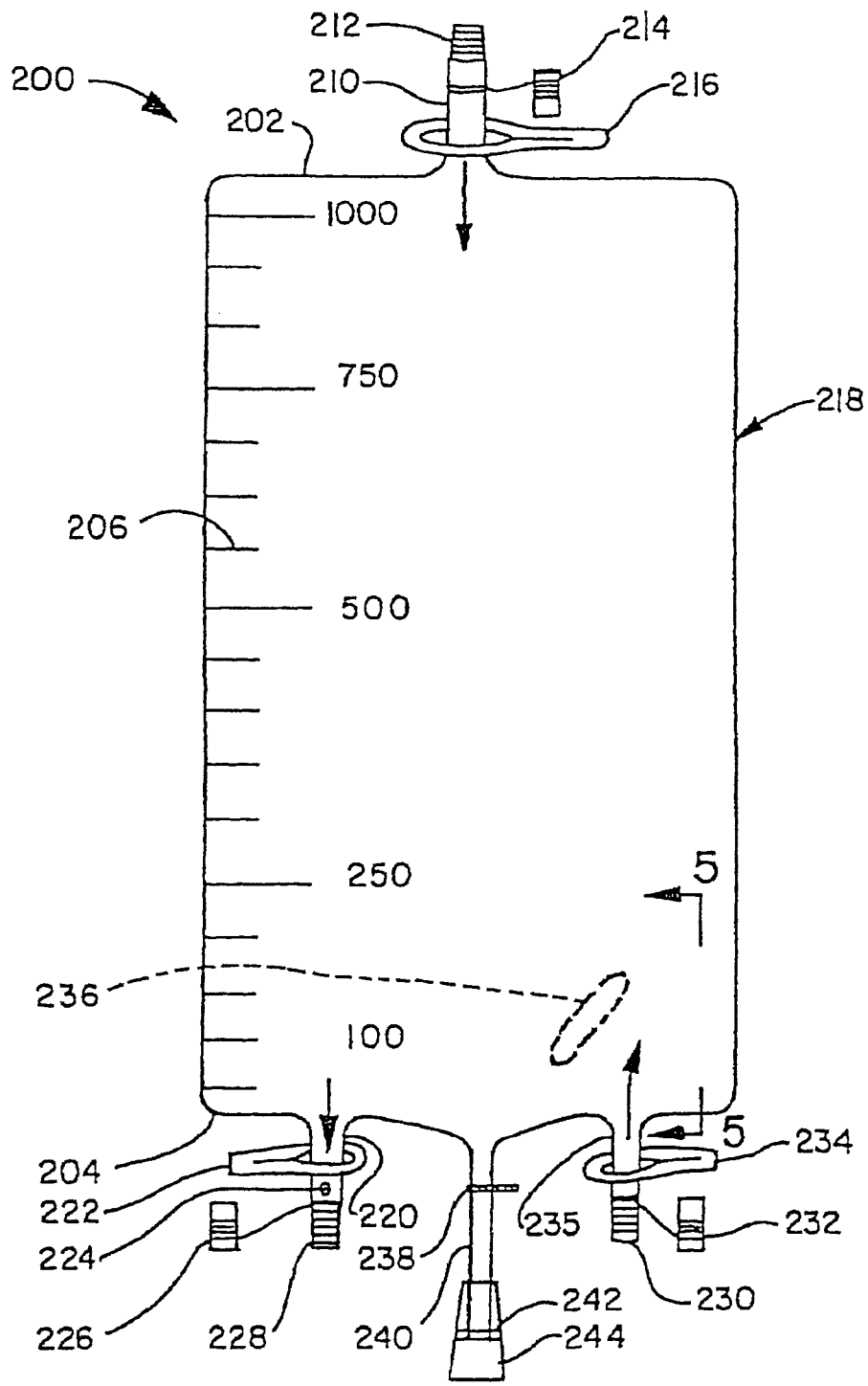
FIGS. 4 and 5 are elevation and section views of the blood bag shown in FIG. 3, which is the preferred embodiment of the blood reservoir for implementing the present invention.
Figure 5:
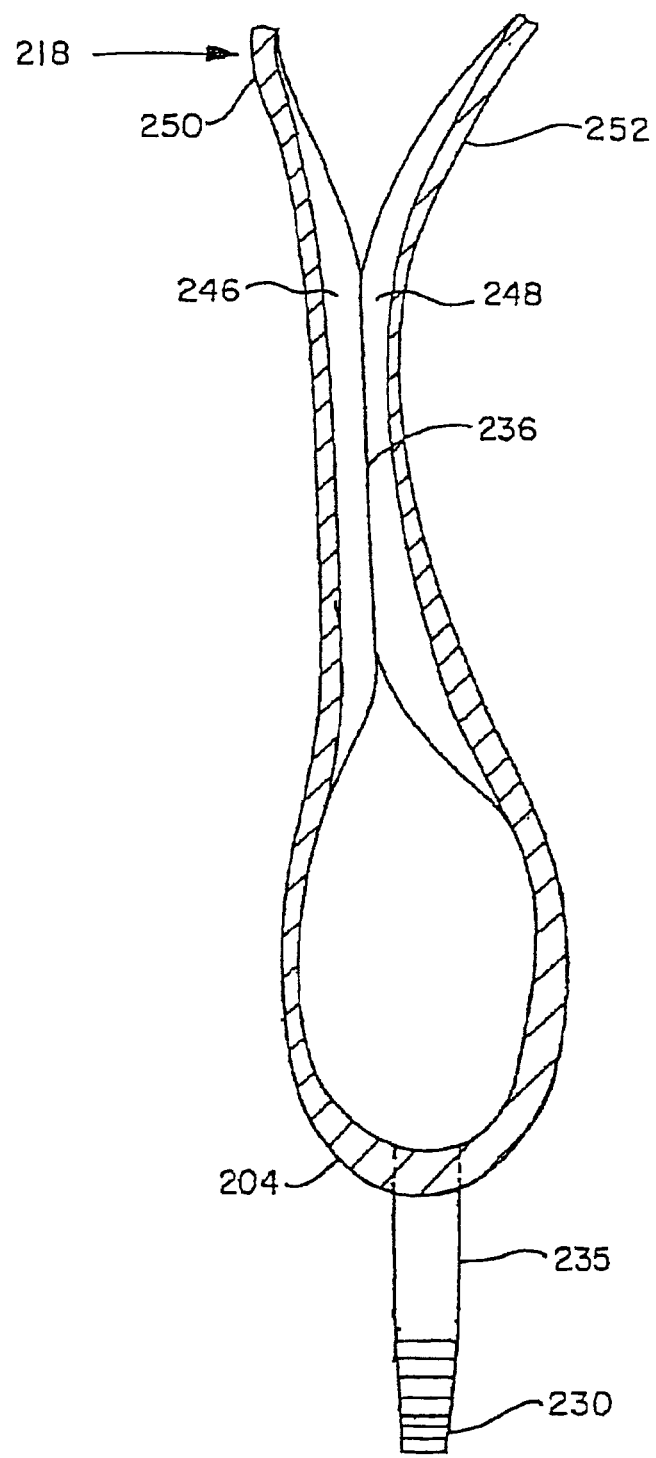

The schematics of FIGS. 3-5, show the present inventor's specially adapted and commercially available Hemobag® container 200 connected to the CPB circuit of FIG. 2, for recovery and hemoconcentration of the fluid in the CPB system after surgery, i.e., after the case. A bag 200 of appropriate size is selected by the perfusionist who will transfer most of the blood in the CPB circuit 118, into the bag 200. The bag 200 with blood is connected to a hemoconcentrating circuit 300, as shown in FIG. 3.

The bag 200 as shown in FIG. 4, is in effect a bag system, comprising a closed, sterile bag 218 of substantially transparent, bio-compatible material, of a type conventionally used for blood storage/and or transfusion, e.g., polyvinyl. Such bags are typically oblong, thereby defining upper (top) and lower (bottom) ends 202,204. The front side of the bag is marked with a scale 206, indicating the approximate volumetric gradations of the content of the bag. Typical bag sizes are 750, 1000 or 2000 milliliter.

An arterial infusion port 210 is situated at the top of the bag, and serves as the conduit for entry of blood from the arterial line 110 of the CPB circuit 118 after the cannulas 102,104 have been removed from the patient. The conduit defining the infusion port 210, terminates in preferably, a stepped and tapered ¼-⅜ inch universal arterial infusion connector 212. A dead end cap 214 and a clip 216 are carried by the conduit, and function therewith in a conventional manner. The clip 216 is preferably a so-called master clip, which can also serve as a hanger for the Hemobag, after it has been filled with blood.

At the lower end 204 of the bag 218, an outlet port 220 is defined by preferably, a ¼ inch conduit on which a clip 222 is carried. Preferably, a ¼ inch Luer connector 224 is connected to the conduit 220, or formed integral therewith, for selectively admitting a flow of air or fluid bidirectionally for reasons to be discussed more fully below. A ¼ inch connection 228 extends below the Luer 224, and a dead end cap 226 is carried thereon.

An inlet port 235 is also situated in spaced relation from the outlet port 220, at the bottom or lower end of the bag. The inlet port is typically defined by a conduit having a ¼ inch end connector 230, and a dead end cap 232. A clip 234 is carried by the inlet conduit 235.

An intravenous IV line 240 is also situated at the lower end of the bag. This is a conventional large bore IV line, having a clip 238 and a terminal female connector 242 for receiving a male IV spike when the contents of the bag are to be reinfused to the patient. The IV line 240 is preferably situated between the outlet port 220 and the inlet port 235 and has a sterile cap 244.

When the bag 200 as depicted in FIG. 4, is set up, the inlet clip 222 and cap 226, outlet clip 234 and cap 232, and IV clip 238 and cap 244 are placed in the closed condition, whereas the infusion clip 216 and cap 214 are open. A connection with the arterial cannula 102 or the arterial line 110, which is typically a ¼ or ⅜ inch line, is then inserted or secured to the universal connector 212 at the infusion port 210 of the bag using spare tubing. The venous cannula 104 is detached from line 108, and a crystalloid solution, is introduced as shown at 158, into line 108. This chases the blood in the CPB circuit 118, along line 108, through the venous reservoir 112, the pump 106 and the remaining components, whereby most of the patient's blood in the CPB circuit 118, is chased into the bag 200. As an alternative, crystalloid solution can be introduced at the venous reservoir 112, via line 160, as a more convenient way of chasing most, but not all, of the blood in the CPB circuit 118 into the bag 200.

When the bag 200 has been filled, the infusion port 210 is closed using the clip 216 and cap 214. Reconnection of the arterial and venous lines with the appropriate size Luer connector for recirculation can be made. The filled bag is processed by the perfusionist, who will establish the hemoconcentrating circuit 300 as depicted in FIG. 3. The bag can be hung in any convenient manner, via the master clip 216. There are a variety of available circuits of the CPB system 100, other than the arterial circuit 118, which can be disconnected and reconfigured to form the hemoconcentration circuit 300. When available, however, connections are made to a spare roller pump. In the example shown in FIG. 3, the suction circuit 120 of FIG. 2, has been removed from roller pump 122. A new ¼ inch line is connected through the pump 122 from the outlet port 220 of the Hemobag via line portion 310, and line portion 312 is connected between the outlet of the pump 122 and the inlet 306 of a hemoconcentrator 302. The outlet of the concentrator 302 is attached via new line 304, to the inlet port 235 of the bag. The hemoconcentrator 302 can be of any conventional configuration, e.g., such as is available as Model HF5000 from Fresenius Medical Care North America, Waltham, Mass. In such hemoconcentrators, a flow of effluent is discharged at 308. The effluent at 308 is removed and only the hematocrit-enriched concentrated whole blood is delivered through line 304 to the bag 200.

The Hemobag 200 preferably includes a baffle 236 located inside the bag, and oriented for directing upward flow entering the bag through the inlet port 235, away from the outlet port 220. The baffle 236 assures even mixing of blood which has been received from the hemoconcentrator 302, with the less concentrated blood in the bag. In particular, the baffle 236 is located closer to the inlet port 235 than to the IV line 240 thereby blocking lateral flow of the concentrated blood when it enters the bag. FIG. 5 shows the baffle 236 as formed by pinching and heat sealing together, portions 246,248 of the front 250 and back 252 walls of the bag 218. Alternatively, a distinct, oblong member (not shown) could be fixed between the walls, preferably at an angle to the vertical.

When the blood in the hemoconcentration circuit 300 reaches an appropriate concentration of hematocrit (for example, as represented by the percent volume reduction from the time circulation in configuration 300 was initiated), the roller pump 122 is stopped and outlet port 220 is closed via clip 222. A flow of air or crystalloid solution is introduced through Luer 224, which is below the clip 222, such that the fluid in line 310, pump 122, hemoconcentrator 302, and line 304 is deprimed and chased back into the bag 200, by pumping through inlet port 235, and the pump 122 is turned off. The clip 234 then closes port 235, and lines 310 and 304 are disconnected from the end connectors 228 and 230. At this point, all clips 216,222 and 234 are closed, and the respective dead end drip caps 214,226 and 232 can be secured to the respective end connectors 212,228 and 230. Line 240 has remained closed by clip 238, and sterile by cap 244.

Although it is preferable that hemoconcentration occur in the operating room adjacent to the field, without undermining the integrity of the CPB circuit, this is not absolutely necessary. For example, the bag can be taken out of the operating room, and hemoconcentration achieved at a different time and different place. Nevertheless, it is contemplated that in most operating rooms, the hemoconcentration will be completed and the Hemobag with concentrated blood will be available for reinfusion, during the time period when the patient is in the operating room.

FIGS. 6-10 show equipment configurations associated with the present invention. An extracorporeal blood circulation system (ECC) 320 includes a venous cannula line 324 having an inlet 326 for drawing oxygen deficient blood from the patient, and an oxygenator 330 in fluid communication with the outlet 328 of the venous cannula, having an inlet 332 for receiving oxygen deficient blood and an outlet 334 for oxygenated blood, and an arterial cannula line 336 having an inlet 338 in fluid communication with the outlet 334 of the oxygenator and an outlet 340 for delivering oxygenated blood to the patient. An arterial pump 342 has an inlet 344 connected to the outlet 328 of the venous line 324 and an outlet 346 connected to an inlet line 332 of the oxygenator 330, for inducing blood flow through the venous cannula line 324, oxygenator 330, and arterial cannula line 336. An arterial filter 335 is preferably provided after the oxygenator 330.

A blood reservoir 348 has an inlet line 350 connected to the outlet 346 of the pump and an outlet line 352 connected to the inlet 344 of the pump. The reservoir has a thrombo-resistant or other biocompatible coating on the inside surface. Flow control means 354-360, such as manually or solenoid operated clamps, valves, or the like, can be opened (shown as open circle) or closed (shown with "X") to permit or block flow, respectively. The four clamps or the like permit selective configuring of at least three blood flow paths.

Figure 6:
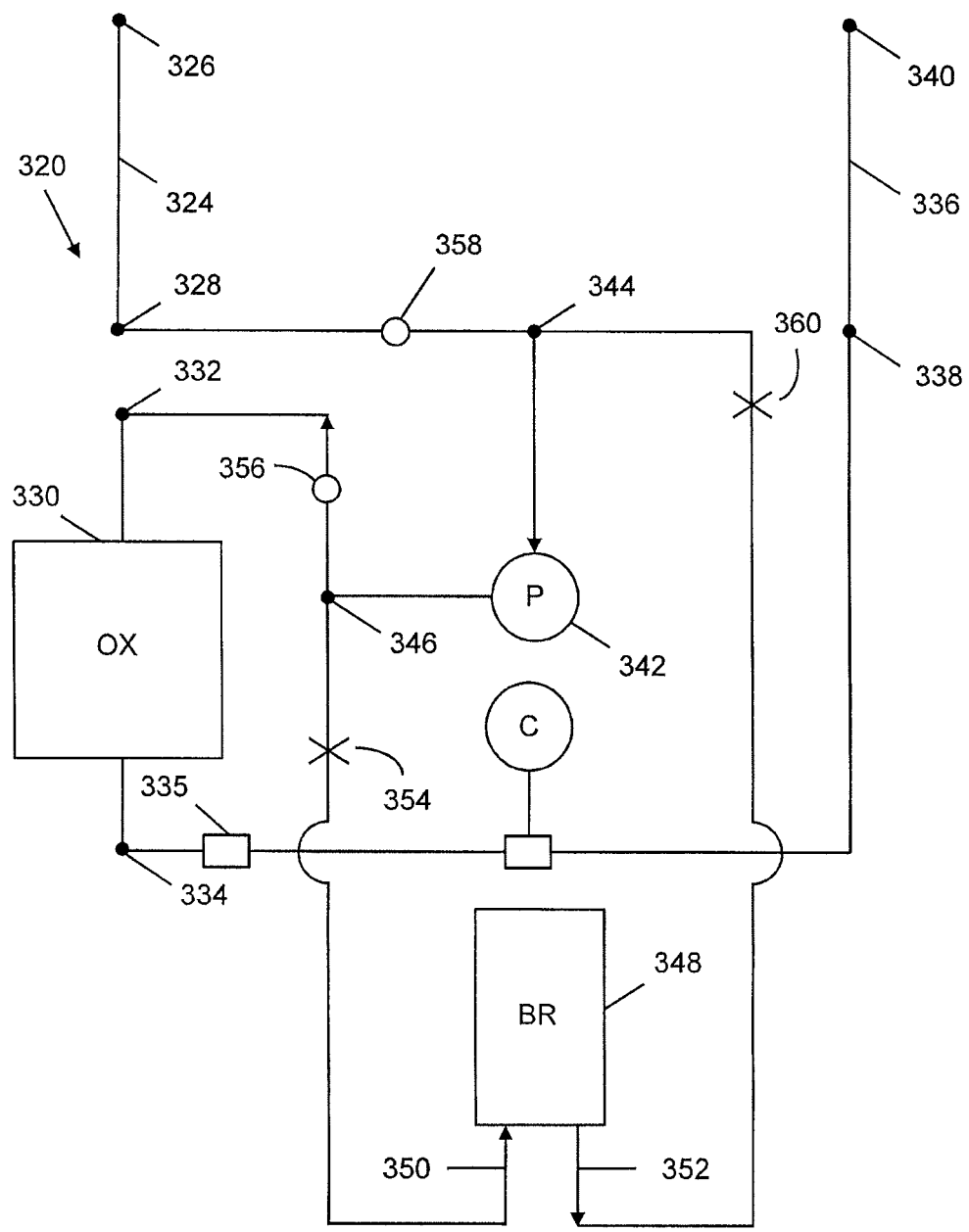
FIG. 6 is a schematic of one aspect of the invention, in which a blood reservoir replaces a conventional venous reservoir, configured in a main path for direct flow of deoxygenated blood from the venous cannula line, through an arterial pump to an oxygenator and return to the patient through an arterial cannula.

FIG. 6 shows a main path in which the inlet 350 and outlet lines 352 of the blood reservoir 348 are blocked at 354 and 360 while pumped blood flows through the venous cannula line 324, the oxygenator 330, and the arterial cannula line 336.

Figure 7:
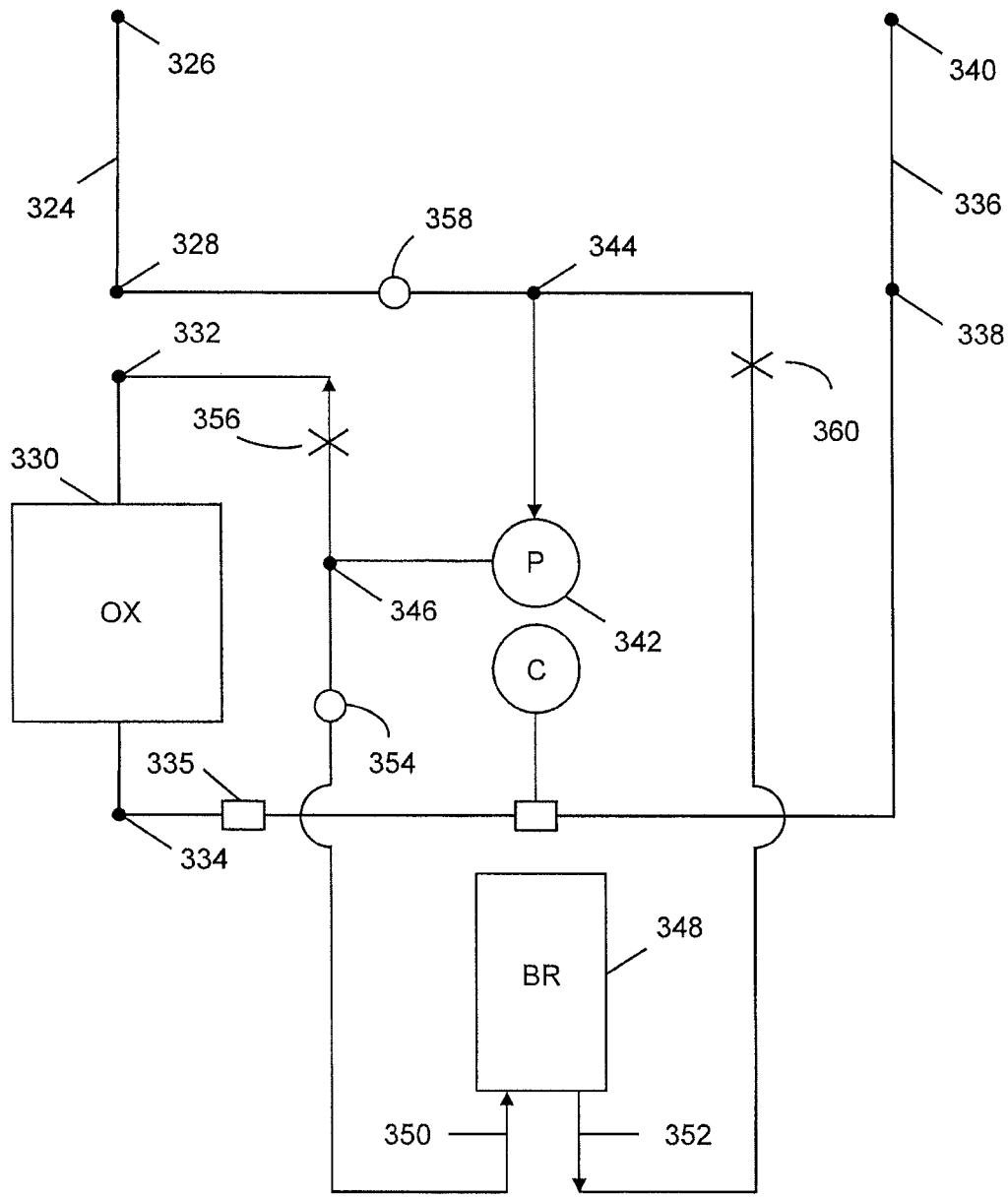
FIG. 7 is a schematic of the system shown in FIG. 6, configured in an accumulator path by which fluid in the venous cannula line flows to the blood reservoir while bypassing the oxygenator.

FIG. 7 shows an accumulator path in which the inlet to the oxygenator 332 and the outlet line of the blood reservoir 352 are blocked at 356 and 360 while blood flows through the venous cannula line 324 and the inlet line to the blood reservoir 350 (with or without the pump operating).

Figure 8:
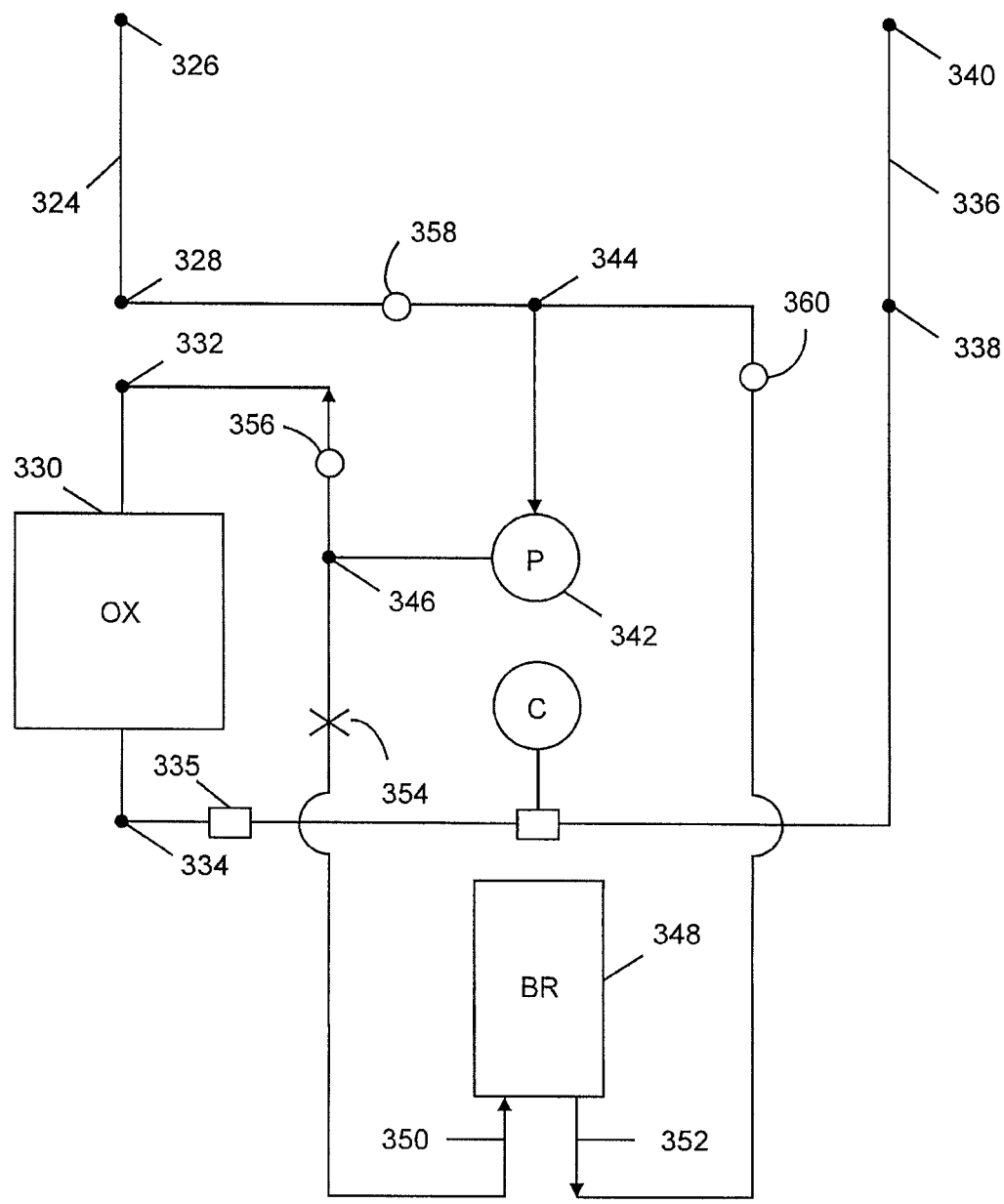
FIG. 8 is a schematic of the system of FIG. 6, configured in a discharge path by which fluid in the blood bag is added to the flow into the pump from the venous cannula line for delivery to the oxygenator.

FIG. 8 shows a discharge path in which the inlet line of the blood reservoir 350 is blocked at 354 while the outlet line 352 of the blood reservoir is open at 360 whereby blood from the blood reservoir 348 flows with pumped blood from the venous cannula line 324 into the oxygenator 330 and the arterial cannula line 336.

Figure 9:
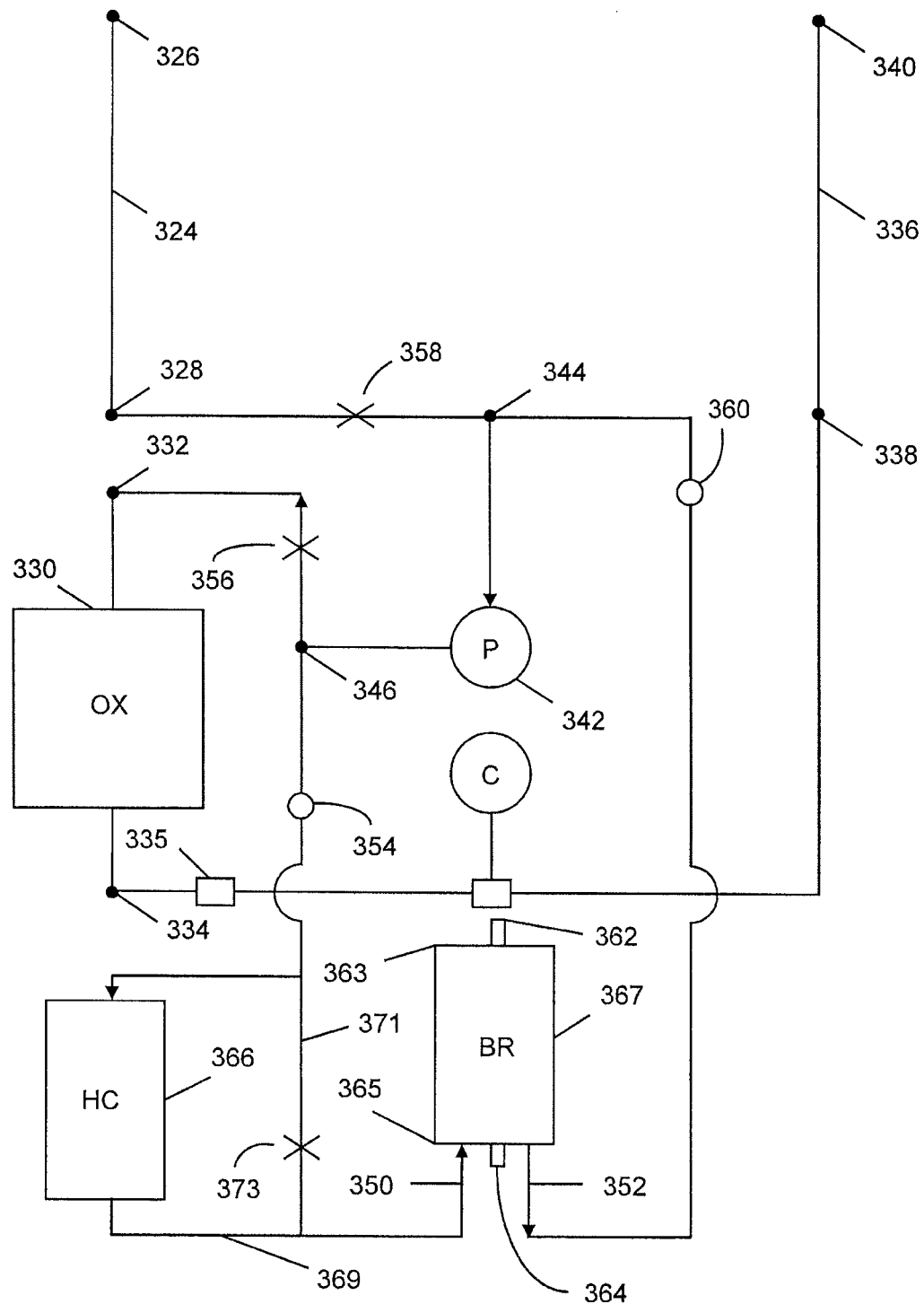
FIG. 9 is a schematic of the system of FIG. 6, in a recovery path configured to hemoconcentrate the fluid in the blood reservoir after the case.

FIG. 9 shows the preferred embodiment with Hemobag including an infusion port 362 located at the upper end 363 of the bag 367, an IV port 364 located at the lower end 365 of the bag 367, and a system configuration by which the fluid in the system is hemoconcentrated. In a preceding step, the clamps 354-360 are configured so that the system fluid is pumped or drained into the reservoir 367. The reservoir 367 would typically have a volume capacity that exceeds that of the remainder of the system, e.g., the blood reservoir 367 should have a capacity of about two liters whereas the fluid volume of the rest of the ECC system would typically be about 1.0 to about 1.5 liters.

The flow control clamps 354-360 are then configured into a recovery path in which the venous cannula line 324 and the oxygenator inlet line 334 are blocked at 356 and 358 while the blood reservoir inlet line 350 is open to bypass line 369 while line segment 371 is closed at 373 and outlet line 352 is also open at 360. A hemoconcentrator 366 is fluidly connected between the outlet of the pump 346 through open clamp 354 and the inlet line of the blood reservoir 350, thereby establishing a recirculating flow of blood between the blood reservoir 367 and the hemoconcentrator 366.

In the embodiment of FIGS. 6-8, the blood reservoir 348 does not have an infusion port 362 at the top or an IV port 366 at the bottom, but the hemomocentration according to FIG. 9 can be achieved using only the inlet 350 and outlet 352 ports.

However, if the blood reservoir with hemoconcentrated blood is to be used directly for reinfusion, the IV port 364 is necessary.

Figure 10:
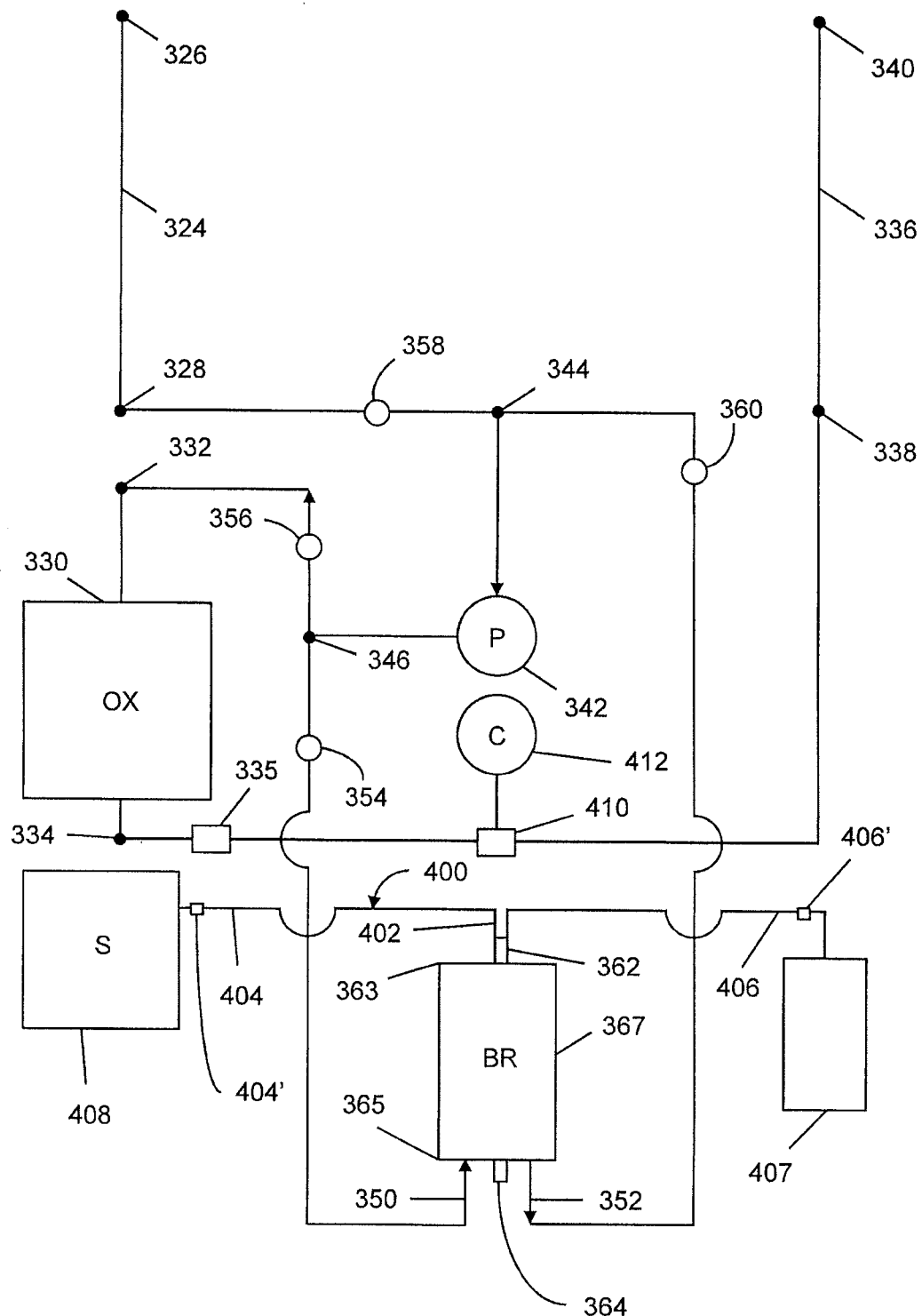
FIG. 10 is a schematic of a further preference, whereby the infusion port at the upper end of the blood reservoir is connected to "Y" tubing through which fluid volume makeup can be added to the system and air can be vented from the system.

FIG. 10 shows the embodiment 400 in which the infusion port 362 is used for makeup volume and venting. The common line 402 of a split line (such as "Y" tubing) is connected to the infusion connector 362, having first 404 and second branches 406. The first branch line 404 has a spike connector 404' fluidly connected to a line from a source of volume makeup fluid 408 into the reservoir. The second branch line 406 is an air evacuation line from the reservoir, which may remain open or have an associated spike or ¼ inch connector 406' if the air is to pass through an extension line into an empty bag 407 or suction. An air detector 410 and vent controller 412 can also be provided.

Although the described system can be configured with any arterial pump 342 that is present in the extracorporeal circuit, a centrifugal pump is preferred because the circuit can be passively drained into the blood reservoir without disengaging the pump (as is required for positive displacement pumps such as roller pumps).

Figure 11:
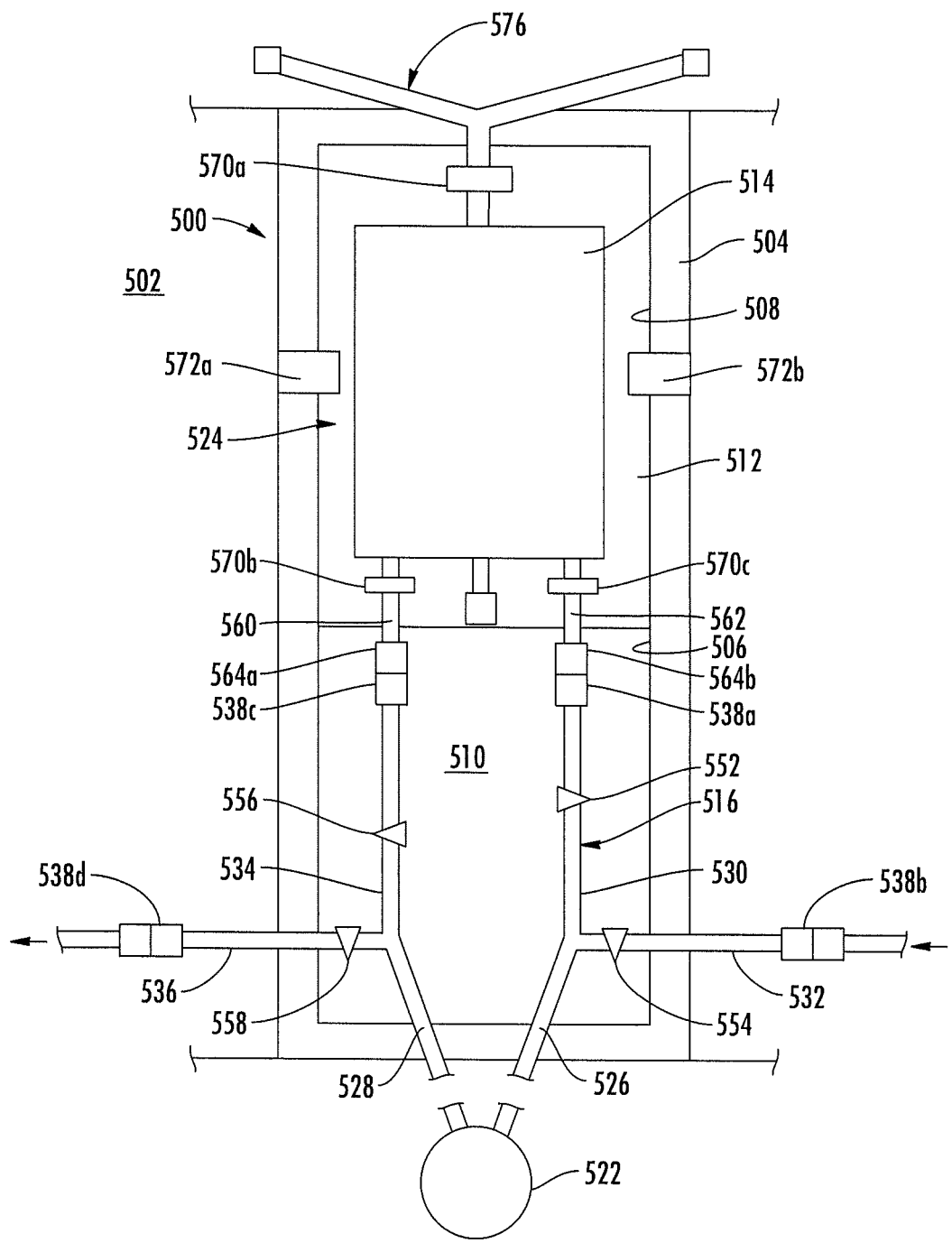
FIG. 11 is a schematic of one way of modular mounting the pump tubing set and the blood reservoir to each other and to the front panel of a heart lung machine.
Figure 12:
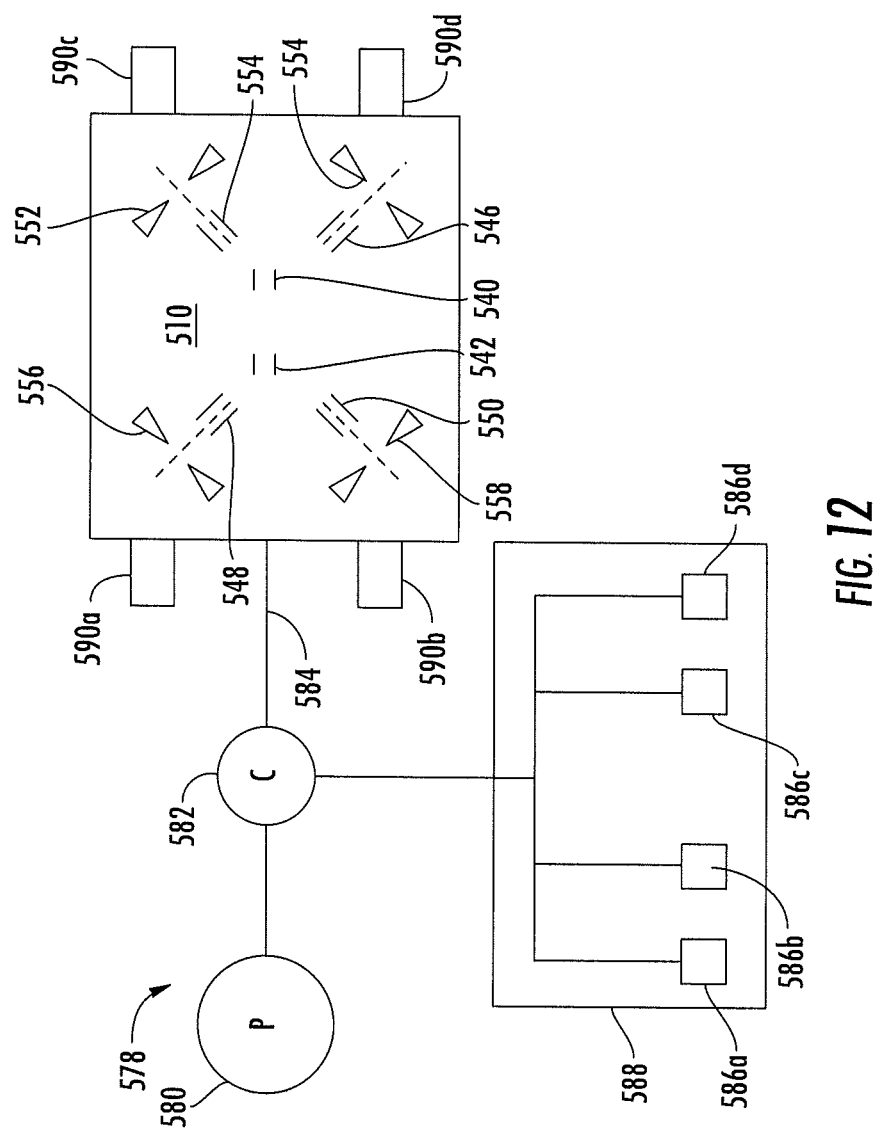
FIG. 12 is a schematic of a recessed portion of the front panel and an associated flow controller, before receiving the pump tubing set.
Figure 13:
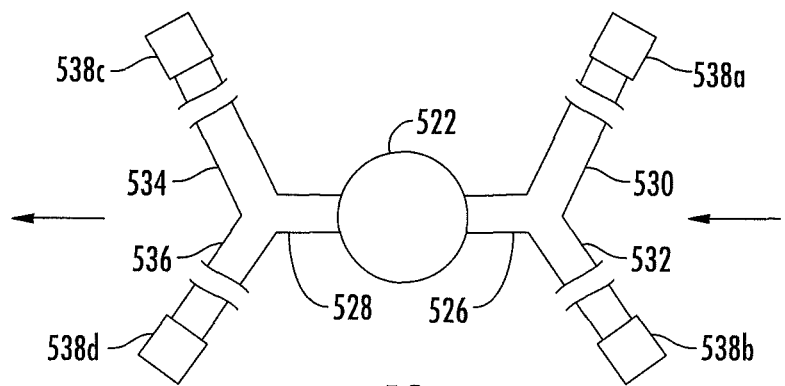
FIG. 13 is a schematic of the pump tubing set before installation in the panel recess shown in FIG. 12.

FIGS. 11-14 show the preferred hardware implementation for achieving the functionality described with respect to FIGS. 6-10. A portion 500 of one machine 502 includes an insert or frame 504 which, in the illustrated embodiment has an inner perimeter 506 defining a recessed region 510 and another inner perimeter 508 defining another recessed region which, in FIG. 11, has a substantially flat support plate 512 and associated blood reservoir bag 514 installed therein. In the lower portion 510, a pump tubing insert 516 is removably mounted. The tubing assembly 516 as shown in FIG. 13 is connected to pump 522.

In the illustrated embodiment, the support plate 512 and reservoir 514 carried thereon form a unit 524 which is inserted in the upper perimeter 508.

The tubing assembly 516 as shown in FIG. 13, is connected to the inlet and outlet side of pump 522, by inlet side common tubing 526 and outlet side common tubing 528 through which fluid normally flows in the direction of the arrows. The inlet tubing 526 can receive fluid through one or both of branch lines 530 and 532, and likewise outlet tubing 528 can deliver fluid through one or both branch lines 534 and 536. Each of these branch lines has a free end with associated connector 538a (Colder), 538b (¼ or ⅜ inch), 538c (Colder), 538d (¼ or ⅜ inch). The installation of the pump insert 516 will be first described with reference to FIGS. 12 and 13. Each of the inlet, outlet and branches is pressed into a suitable guide, indicated at 540, 542, 544, 546, 548, and 550, respectively. The branches 530, 532, 534 and 536 are also inserted in clamping members 552, 554, 556 and 558 respectively. Each clamping member can be actuated by a pair of solenoids, or one clamping surface can be stationary while only the other is actuated, whereby flow through the branches can be selectively opened or closed.

Figure 14:
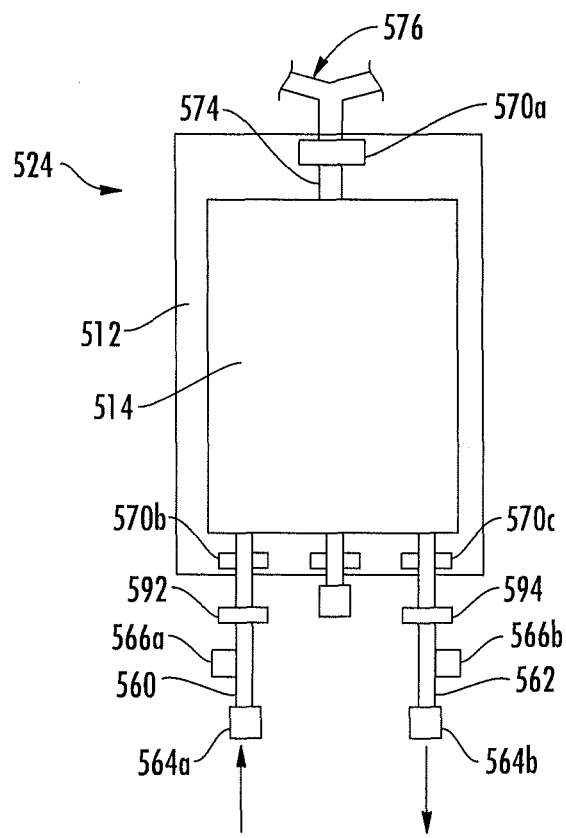
FIG. 14 is a schematic of the reservoir unit before installation on the front panel shown in FIG. 11.

When the reservoir unit 524 is inserted into the opening 508, it can be clamped therein with pivoting or other spring loaded locks such as shown at 572a, 572b in FIG. 11. As shown in FIG. 14, the reservoir has an inlet line 560 and an outlet line 562 with respective Colder connectors 564a and 564b. The inlet and outlet lines preferably have Luers 566a and 566b. Preferably, an IV transfusion line with associated spike connector is also provided as shown at 568. The bag may be secured to the support plate 512 by pivoting or spring loaded locks 570a, 570b and 570c. Preferably, the bag also has an infusion line 574 with a "Y" type connection 576 and the upper portion of the bag can be held in place by the lock 570a acting on the infusion line 574.

As shown in FIG. 11, the overall system is configured such that the connector 538c on outlet branch 534 of the pump mates with connector 564a on the inlet line to the reservoir 514. Similarly, the connector 538a on the pump inlet branch 530 is mated with connector 564b on the outlet line 562 of the reservoir.

This arrangement and associated clamps 552, 554, 556, and 558 permit a variety of flow configurations. In general, however, a primary flow from the venous cannula enters pump inlet branch 532 through the connection at 538b, and is delivered to the oxygenator in the pump outlet branch 536 at connector 538d. A parallel flow loop can also be formed with flow from the pump 522 through outlet branch 534 into reservoir inlet line 560, through the reservoir 514, out the reservoir outlet line 562 and back to the pump through pump inlet branch 530. In an automated system electronic controls would likewise be built-in, including a power source 580, a control logic at 582, with signal lines indicated generally at 584 going to the respective four solenoids of the four clamps. A display 588 of digitally or electro-mechanically connected set of switches or the like 586a-586d for either opening or closing the respective clamps and thereby configure the various available flow paths evident from FIG. 11.

The component shown in FIG. 12 can be carried on another support plate or the same support plate as indicated at 512 in FIG. 14. The plate could be locked to a frame using pivoting, spring loaded or similar locks such as shown at 590a-d. The clamps could be mounted on the plate but manually operated. Alternatively, the plate could only have the guides whereas the branches of the pump insert would carry manually operated clamps. Based on the present disclosure, one of ordinary skill can readily design alternatives falling within the scope of the invention, in which all, a portion, or none of the pump is carried by the pump insert.

The various flow configurations have been described with respect to FIGS. 6-10. In that embodiment, the blood reservoir 514 is removed from the support plate 512 after closing clamps 592 and 594 (as shown in FIG. 14), whereupon the reservoir 514 is connected in a hemoconcentration circuit via connectors 564a, 564b. In another embodiment, hemoconcentration can be performed while the reservoir is on the support 512 and still fluidly connected to the pump tubing set 516, by connecting the inlet and outlet of the hemoconcentrator and tubing associated with a different pump, to the Luers 566a, 566b of the inlet line 560 and outlet line 562 of the reservoir 514.

The system is also valuable as part of the ECC used with patients in critical care areas, which may require continuous connection to a ECC over a period of several days, where fluid volume management as well as autologous blood recovery are improved relative to known techniques. Such long term configuration may or may not include an oxygenator, and the cannulas from and to the patient may be situated in locations other than standard venous and arterial blood vessels.

The invention claimed is:

1. An extracorporeal blood circuit system (ECC) for use on a patient, comprising
a venous cannula line having an inlet and an outlet;
an oxygenator in fluid communication with the outlet of the venous cannula line, having an inlet for receiving oxygen deficient blood and an outlet for oxygenated blood;
an arterial cannula line having an inlet in fluid communication with the outlet of the oxygenator and an outlet for delivering oxygenated blood;
a pump having a split inlet with one branch connected to the outlet of the venous line and a split outlet with one branch connected to an inlet line of the oxygenator, for inducing blood flow through the venous cannula line, oxygenator, and arterial cannula line:
a blood reservoir having an inlet line connected to another branch of the split outlet of said pump and an outlet line connected to another branch of the split inlet of said pump;
a plurality of flow control means for selectively configuring at least three blood paths for flowing blood delivered by said pump,
a main path in which the inlet and outlet lines of the blood reservoir are blocked while pumped blood flows through the venous cannula line, the oxygenator, and the arterial cannula line,
an accumulator path in which the inlet to the oxygenator and the outlet line of the blood reservoir are blocked while pumped blood flows through the venous cannula line and the inlet line to the blood reservoir, and
a discharge path in which the inlet line of the blood reservoir is blocked while the outlet line of the blood reservoir is open whereby pumped blood from the blood reservoir flows into the oxygenator and the arterial cannula line;
wherein
said pump split inlet is connected to and receives all flow from the outlet of the venous line through a first of said control means, and is connected to and receives all flow from the outlet line of the blood reservoir through a second of said control means; and
said pump split outlet is connected to the inlet of the oxygenator through a third of said control means and to the inlet of the blood reservoir through a fourth of said control means
and wherein
the blood reservoir is a closed bag of substantially transparent, bio-compatible material, defining upper and lower ends;
an infusion port is located at the upper end of the bag;
an outlet port is located at the lower end of the bag;
an inlet port is located at the lower end of the bag;
an IV port is located at the lower end of the bag;
a fifth of said control means is situated in a flow line segment between the fourth control means and the inlet line of the blood reservoir;
said plurality of flow control means selectively configures an additional, recovery path in which the venous cannula line and flow to the oxygenator are blocked while the blood reservoir inlet and outlet lines are open; and
a hemoconcentrator is fluidly connected in a flow configuration parallel to said line segment, between the fourth control means and the inlet line of the blood reservoir, thereby establishing a recirculating flow of blood between the blood reservoir and the hemoconcentrator when the first control means, third control means and the fifth control means are closed, and the second control means and fourth control means are open.

2. An extracorporeal blood circuit system (ECC) for use on a patient, comprising
a venous cannula line having an inlet and an outlet;
an oxygenator in fluid communication with the outlet of the venous cannula line, having an inlet for receiving oxygen deficient blood and an outlet for oxygenated blood;
an arterial cannula line having an inlet in fluid communication with the outlet of the oxygenator and an outlet for delivering oxygenated blood;
a pump having a split inlet with one branch connected to the outlet of the venous line and a split outlet with one branch connected to an inlet line of the oxygenator, for inducing blood flow through the venous cannula line, oxygenator, and arterial cannula line:
a blood reservoir having an inlet line connected to another branch of the split outlet of said pump and an outlet line connected to another branch of the split inlet of said pump;
a plurality of flow control means for selectively configuring at least three blood paths for flowing blood delivered by said pump,
a main path in which the inlet and outlet lines of the blood reservoir are blocked while pumped blood flows through the venous cannula line, the oxygenator, and the arterial cannula line,
an accumulator path in which the inlet to the oxygenator and the outlet line of the blood reservoir are blocked while pumped blood flows through the venous cannula line and the inlet line to the blood reservoir, and
a discharge path in which the inlet line of the blood reservoir is blocked while the outlet line of the blood reservoir is open whereby pumped blood from the blood reservoir flows into the oxygenator and the arterial cannula line;
wherein
said pump split inlet is connected to and receives all flow from the outlet of the venous line through a first of said control means, and is connected to and receives all flow from the outlet line of the blood reservoir through a second of said control means; and
said pump split outlet is connected to the inlet of the oxygenator through a third of said control means and to the inlet of the blood reservoir through a fourth of said control means;
and wherein
a fifth of said control means is situated in a flow line segment between the fourth control means and the inlet line of the blood reservoir;
said plurality of flow control means selectively configures an additional, recovery path in which the venous cannula line and flow to the oxygenator are blocked while the blood reservoir inlet and outlet lines are open; and
a hemoconcentrator is fluidly connected in a flow configuration parallel to said line segment, between the fourth control means and the inlet line of the blood reservoir, thereby establishing a recirculating flow of blood between the blood reservoir and the hemoconcentrator when the first control means, third control means and the fifth control means are closed, and the second control means and fourth control means are open.

3. The extracorporeal blood circuit system of claim 2, including a baffle inside the bag, for directing upward flow entering the bag through the inlet port, away from the outlet port.

4. The extracorporeal blood circuit system of claim 2, wherein the pump is a centrifugal pump.

5. The extracorporeal blood circuit system of claim 2, wherein said plurality of control means selectively configures a drain path in which the inlets and outlets of the pump and blood reservoir are all open.

6. The extracorporeal blood circuit system of claim 2, wherein each of said control means is a clamp.

7. The extracorporeal blood circuit system of claim 2, wherein each said control means is a manually actuated clamp.

8. The extracorporeal blood circuit system of claim 2, wherein each of said control means is a solenoid operated clamp.

9. The extracorporeal blood circuit system of claim 2, wherein
said first control means is situated adjacent to both the outlet of the venous cannula line and the pump inlet;
said third control means is situated adjacent to both the pump outlet and the inlet to the oxygenator; and
said second control means is situated adjacent to both the outlet line of the blood reservoir and the inlet to the pump.

10. An extracorporeal blood circuit system (ECC) for use on a patient, comprising
- a venous cannula line having an inlet and an outlet;
- an oxygenator in fluid communication with the outlet of the venous cannula line, having an inlet for receiving oxygen deficient blood and an outlet for oxygenated blood;
- an arterial cannula line having an inlet in fluid communication with the outlet of the oxygenator and an outlet for delivering oxygenated blood;
- a pump having an inlet connected to the outlet of the venous line and an outlet connected to an inlet line of the oxygenator, for inducing blood flow through the venous cannula line, oxygenator, and arterial cannula line;
- a blood reservoir having an inlet line connected to the outlet of said pump and an outlet line connected to inlet of said pump;
- a plurality of flow control means for selectively configuring at least three blood flow paths,
  - a main path in which the inlet and outlet lines of the blood reservoir are blocked while pumped blood flows through the venous cannula line, the oxygenator, and the arterial cannula line,
  - an accumulator path in which the inlet to the oxygenator and the outlet line of the blood reservoir are blocked while blood flows through the venous cannula line and the inlet line to the blood reservoir, and
  - a discharge path in which the inlet line of the blood reservoir is blocked while the outlet line of the blood reservoir is open whereby blood from the blood reservoir flows into the oxygenator and the arterial cannula line;
- wherein
  - said pump inlet is connected to and receives all flow from the outlet of the venous line through a first of said control means, and is connected to and receives all flow from the outlet line of the blood reservoir through a second of said control means; and
  - said pump outlet is connected to the inlet of the oxygenator through a third of said control means and to the inlet of the blood reservoir through a fourth of said control means;
- a fifth of said control means is situated in a flow line segment between the fourth control means and the inlet line of the blood reservoir;
- said plurality of flow control means selectively configures an additional, recovery path in which the venous cannula line and flow to the oxygenator are blocked while the blood reservoir inlet and outlet lines are open; and
- a hemoconcentrator is fluidly connected in a flow configuration parallel to said line segment, between the fourth control means and the inlet line of the blood reservoir, thereby establishing a recirculating flow of blood between the blood reservoir and the hemoconcentrator when the first control means, third control means and the fifth control means are closed, and the second control means and fourth control means are open.

11. The extracorporeal blood circuit system of claim 10, wherein the pump is a centrifugal pump.

12. The extracorporeal blood circuit system of claim 10, wherein said plurality of control means selectively configures a drain path in which the inlets and outlets of the pump and blood reservoir are all open.

13. The extracorporeal blood circuit system of claim 10 wherein each of said control means is a clamp.

14. The extracorporeal blood circuit system of claim 10, wherein each of said control means is a manually actuated clamp.

15. The extracorporeal blood circuit system of claim 10, wherein each of said control means includes a solenoid operated clamp.

16. The extracorporeal blood circuit system of claim 10, wherein
- said first control means is situated adjacent to both the outlet of the venous cannula line and the pump inlet;
- said third control means is situated adjacent to both the pump outlet and the inlet to the oxygenator; and
- said second control means is situated adjacent to both the outlet line of the blood reservoir and the inlet to the pump.

17. The extracorporeal blood circuit system of claim 10, wherein
- said one branch of the pump split inlet and said venous cannula are on opposite sides of and adjacent to the first flow control means;
- said one branch of the pump split outlet and said oxygenator inlet are on opposites sides of and adjacent to the third flow control means;
- said other branch of the pump split outlet and said blood reservoir inlet are on opposite sides of and adjacent to the fourth flow control means; and
- said other branch of the pump split inlet and said blood reservoir outlet are on opposite sides of and adjacent to the second flow control means.

18. The extracorporeal blood circuit system of claim 17, wherein each of said flow control means is a clamp.

19. The extracorporeal blood circuit system of claim 10, wherein
- the blood reservoir is a closed bag of substantially transparent, bio-compatible material, defining upper and lower ends;
- an infusion port is located at the upper end of the bag;
- an outlet port is located at the lower end of the bag;
- an inlet port is located at the lower end of the bag; and
- an IV port is located at the lower end of the bag.

* * * * *